US012796961B2

(12) United States Patent
Zenzmaier

(10) Patent No.: US 12,796,961 B2
(45) Date of Patent: Nov. 17, 2026

(54) METHOD FOR CONTINOUS DEFINITION OF THE POSITION OF A PERSON'S PELVIS BY MEANS OF A SINGLE OPERATIONAL SENSOR

(71) Applicant: SANLAS HOLDING GMBH, Graz (AT)

(72) Inventor: Cornelia Zenzmaier, Laßnitzhöhe (AT)

(73) Assignee: SANLAS HOLDING GMBH, Graz (AT)

( * ) Notice: Subject to any disclaimer, the term of this patent is extended or adjusted under 35 U.S.C. 154(b) by 269 days.

(21) Appl. No.: 18/705,791

(22) PCT Filed: Oct. 27, 2022

(86) PCT No.: PCT/AT2022/060371
§ 371 (c)(1),
(2) Date: Jun. 4, 2024

(87) PCT Pub. No.: WO2023/070141
PCT Pub. Date: May 4, 2023

(65) Prior Publication Data

US 2026/0137303 A1 May 21, 2026

(30) Foreign Application Priority Data

Oct. 29, 2021 (AT) .............................. A 50858/2021

(51) Int. Cl.
*A61B 5/11* (2006.01)
*A47C 31/12* (2006.01)
*A61B 5/00* (2006.01)

(52) U.S. Cl.
CPC .......... *A61B 5/1116* (2013.01); *A47C 31/126* (2013.01); *A61B 5/1126* (2013.01); (Continued)

(58) Field of Classification Search
None
See application file for complete search history.

(56) References Cited

U.S. PATENT DOCUMENTS 6,450,957 B1 9/2002 Tomohisa et al.
2013/0015976 A1* 1/2013 Chang ................. A61B 5/1121 340/573.7

(Continued)

FOREIGN PATENT DOCUMENTS

AT 523112 A1 5/2021
CN 111616845 A 9/2020

(Continued)

OTHER PUBLICATIONS

English Translation of CN111616845A (Year: 2020).*

(Continued)

*Primary Examiner* — Etsub D Berhanu
(74) *Attorney, Agent, or Firm* — Workman Nydegger

(57) ABSTRACT

A method of continuously determining the orientation of a person's pelvis using a single deployment sensor, the method including the operations: providing a calibration sensor and the deployment sensor, applying the deployment sensor to the person's body in the area of the pelvis, positioning the person on the calibration sensor, in a computing unit, receiving measured values of the calibration sensor and determining a reference depiction of the pelvis based on the measured values received from the calibration sensor, in the computing unit, receiving measured values of the deployment sensor, and updating the current orientation of the pelvis based only on the measured values received from the deployment sensor.

14 Claims, 4 Drawing Sheets

(52) U.S. Cl.
CPC .......... *A61B 5/4566* (2013.01); *A61B 5/6891* (2013.01); *A61B 2562/0247* (2013.01)

(56) References Cited

U.S. PATENT DOCUMENTS

| | | | | |
|---|---|---|---|---|
| 2014/0303524 | A1 | 10/2014 | Chen et al. | |
| 2016/0296160 | A1* | 10/2016 | Larson | A61G 7/057 |
| 2016/0331280 | A1* | 11/2016 | Huldt | A61B 5/6838 |
| 2018/0140229 | A1 | 5/2018 | Kesaniemi | |
| 2019/0239813 | A1* | 8/2019 | Sai | A61B 5/1036 |
| 2022/0167876 | A1 | 6/2022 | Kaltenbach et al. | |

FOREIGN PATENT DOCUMENTS

| | | | | |
|---|---|---|---|---|
| JP | 2003111646 | A * | 4/2003 | A47C 31/126 |
| WO | 2020/182962 | A1 | 9/2020 | |
| WO | 2020/215109 | A1 | 10/2020 | |
| WO | 2021/072461 | A1 | 4/2021 | |
| WO | 2021/152847 | A1 | 8/2021 | |

OTHER PUBLICATIONS

Van Geffen et al. Decoupled pelvis rotation in sitting: A passive motion technique that regulates buttock load associated with pressure ulcer development. Journal of Biomechanics. 42 (2009) 1288-1294. (Year: 2009).*
English Translation of JP2003111646A (Year: 2003).*
International Search Report and Written Opinion, mailed Feb. 20, 2023, from PCT International Application No. PCT/AT2022/060371, 23 pages.

* cited by examiner

METHOD FOR CONTINOUS DEFINITION OF THE POSITION OF A PERSON'S PELVIS BY MEANS OF A SINGLE OPERATIONAL SENSOR

The invention relates to a method of continuously determining the orientation of a person's pelvis using a single deployment sensor for determining a translatory change in a spatial position and a rotatory change in a spatial orientation.

A person's pelvis is considered to be a position controller for a neutral orientation of the functional spine and the lower extremities. Although the pelvis has age-and gender-specific differences in terms of aspect and angular ratios, a universally valid, uniform description of the orientation-related strain thereof as well as a clearly characterizable classification of the pelvic orientation in different posture situations, in particular the upright standing, the upright sitting and the horizontal lying positions, can still be provided. In particular, the strain situation in the lowest lumbar spine region can be positively influenced, among other things, by precise pelvic statics.

People are often not aware of their own individual posture when standing, sitting and lying down and adopt positions that can cause one-sided painful muscle contractures and, in the long run, can lead to attrition processes, including herniated discs, in the event of incorrect loading of the spine and pelvis structure, especially in the transition areas thereof, the sacroiliac joints. In particular, sitting for long periods of time requires permanent static work from the muscles, often in a false posture and without sufficient compensatory movements, which causes muscular imbalances and promotes a wide range of physical complaints, also in the extremities.

In order to be able to evaluate incorrect postures of the spine and also subsequently correct them through targeted measures, it must be determined at the beginning in which position or, respectively, orientation the pelvis is currently in relation to a reference system (e.g., horizontal and vertical planes for the standing and lying positions, seating systems with different seat angles for sitting postures). This problem is known per se from the prior art and can be solved, for example, by observing the characteristic points of the pelvis in order to measure the pelvis and its orientation. In this case, however, the characteristic points must be continuously monitored and tracked in order to detect any change in the position or, respectively, orientation of the pelvis.

From AT 523 112A 1, it is furthermore known to provide a seat or, respectively, a lounger, with surface sensors, i.e., pressure sensors, being installed in the seating area or the backrest. When a person sits down on this seat or, respectively, lies down on this lounger, peak pressures can be determined that can be attributed to the characteristic points of the pelvis in their mutual geometric correlation and, always in the same way, to the person. In particular, the characteristic positions of the ischial tuberosities, the coccyx-sacrum joint, the sacrum in the area of the sacroiliac joints with the iliac crests, as well as the pubic bone and the iliac spines of the person can be determined. Using this method, a current determination of the location and orientation of the pelvis can be done by the surface sensor in a highly precise manner as long as the person sits on the seat or lies on the lounger and the conditions of use allow the use of surface sensors in a seating or reclining system or, respectively, their integration therein. Due to the high geometric resolution of the sensors, this method is also suitable, for example, as an external system for calibration, as changes in all three body levels can be reliably evaluated. In addition, it is possible to determine minimal changes in the location and orientation of the pelvis in very limited measuring ranges, thus ensuring precise pelvic statics.

However, the method of AT 523 112 A1 is very limited, since the determination of the location and orientation of the pelvis can only be performed if the person is in a predominantly passive posture situation, or an auxiliary function can be fulfilled by using large-scale surface sensors (e.g., pressure monitoring for pressure ulcer prevention).

The objective of the invention is to overcome such limitations of the prior art and to enable a dynamic determination of the location and orientation of the pelvis relative to a defined reference system, which is possible even if the person is in a prone position, in a supine position or in a severe malposition, or in dynamic posture situations.

With the method according to the invention, a measuring method for assessing all posture situations, which can be compared to each other, is thus provided.

This objective is achieved by a method of continuously determining the orientation of a person's pelvis using a single deployment sensor, comprising the steps of:

- providing at least one calibration sensor and the deployment sensor,
- applying the deployment sensor to the person's body in the area of the pelvis, in particular in the area of a characteristic point of the pelvis such as the pubic bone, the iliac crest, the iliac spine or the sacrum,
- positioning the person on the at least one calibration sensor or applying the at least one calibration sensor to the person,
- in a computing unit, receiving measured values of the calibration sensor and determining a reference depiction of the pelvis based on the measured values received from the calibration sensor, with the current orientation of the pelvis being stored as the original orientation,
- in the computing unit, receiving measured values of the deployment sensor, and updating the current orientation of the pelvis based only on the measured values received from the deployment sensor.

The method according to the invention has the advantage that a precise determination of a reference depiction with several calibration sensors or, respectively, one or several planar calibration sensors has to occur only at the beginning, whereupon the further dynamic tracking of the pelvis can be performed using a single sensor. In this way, the calibration sensors can even be removed or, respectively, the person can get up from a seat with a surface sensor and the dynamic tracking of the orientation of the pelvis can be continued.

Since the person does not have to wear more than one sensor after the first analysis of the pelvis, higher wearing comfort and significantly greater freedom of movement will arise for the person. For example, the person can easily switch from a prone position to a supine position without the need to perform the measuring process once again with the numerous or, respectively, complex calibration sensors.

In this case, the deployment sensor according to the invention can be designed as a simple inertial measurement unit, e.g., comprising a rotational speed sensor and, if necessary, also an acceleration sensor. Such sensors can have a very small design, as is known, for example, from smartphone technologies, so that the person's freedom of movement is not impaired by the deployment sensor, wherein constant tracking of the current orientation of the pelvis and, optionally, also of the current location of the pelvis can still be continued. For example, if the deployment sensor is provided with an adhesive or is incorporated into a plaster or adhesive strip, and/or communicates wirelessly with the computing unit, the deployment sensor can even be worn under clothing.

It should be noted that another finding of the invention is that, depending on the application, it may be sufficient to track only the current orientation of the pelvis, rather than the current location of the pelvis. For example, the person can sit on the calibration sensor, get up after determining the reference depiction and sit down on another seat. According to the invention, it is not absolutely necessary to track the location of the pelvis for determining the posture, even if, for example, there is a different sitting height, since tracking the orientation of the pelvis is sufficient for determining a posture of the person. In the simplest case, the deployment sensor is thus designed only for providing measured values based on which a rotatory change in the point at which the deployment sensor is arranged can be determined. In the simplest case, the deployment sensor can thus only be a rotational speed sensor, for example, and is unable to determine a translatory change in the spatial location. In the very simplest case, it may also be sufficient to determine a rotation about a single spatial direction using the deployment sensor in order to detect a forward and backward tilt of the pelvis, from which a change in the person's posture can already be determined. For this purpose, however, the rotational speed sensor should be arranged centrically on the pelvis. Since this is difficult to implement in practice, a rotational speed sensor is usually used which is able to determine all rotations about all three spatial directions.

In a preferred embodiment, however, not only the orientation of the pelvis can be tracked easily, but also the location. Thus, the invention furthermore relates to a method of continuously determining the location and orientation of a person's pelvis using a single deployment sensor for determining a translatory change in a spatial location and a rotatory change in a spatial orientation, comprising the steps of:

- providing at least one calibration sensor and the deployment sensor, wherein the deployment sensor can be designed especially for detecting the translatory change in the spatial location and the rotatory change in the spatial orientation of the deployment sensor,
- applying the deployment sensor to the person's body in the area of the pelvis, in particular in the area of a characteristic point of the pelvis such as the pubic bone, the iliac crest or the sacrum,
- positioning the person on the at least one calibration sensor or applying the at least one calibration sensor to the person,
- in a computing unit, receiving measured values of the calibration sensor and determining a reference depiction of the pelvis based on the measured values received from the calibration sensor, with the current location and the current orientation of the pelvis being stored as the original location and the original orientation,
- in the computing unit, receiving measured values of the deployment sensor, wherein, optionally, the measured values can directly include the translatory change in the spatial location and the rotatory change in the spatial orientation or can be at a predetermined distance, for example, because of two measurement sets of translatory changes in the spatial location, and updating the current location and the current orientation of the pelvis based only on the measured values received from the deployment sensor.

In this embodiment, the sensor is thus designed for providing measured values from which a rotatory and translatory change in the point at which the deployment sensor is arranged can be determined. For this purpose, the deployment sensor is usually formed by a combination of a rotational speed sensor with an acceleration sensor. Such a sensor combination can be purchased cheaply on the market because it is also widely used in smartphones.

Alternatively, the deployment sensor could be formed by two acceleration sensors at a predetermined distance or by two rotational speed sensors at a predetermined distance, which, when combined, newly form a deployment sensor for translationally changing the spatial location or, respectively, for rotationally changing the spatial orientation.

In all embodiments, however, the deployment sensor is furthermore a substantially point-shaped sensor, preferably having an area of $0.5cm^2$-$10\ cm^2$ when attached to the pelvis, so that it is noticed as little as possible by the user and is not disruptive. It should be emphasized once again that only a single point-shaped deployment sensor needs to be used for tracking the orientation (and, if necessary, the location) of the pelvis.

In the following, variants of the continuous determination of the location and orientation of the pelvis will be addressed one at a time, although a continuous location determination can also be omitted, as explained above.

The calibration sensors for determining the reference depiction or, respectively, the original location and the original orientation can be selected, for example, according to the prior art. In a first variant of the method according to the invention, a surface sensor can be provided as a calibration sensor, for example, with the surface sensor determining the position of at least two, preferably at least three, characteristic points of the pelvis from measured pressure readings and, from this, the reference depiction.

In this case, the surface sensor can be part of a seat element and/or a back element, wherein the seat element or, respectively, the back element can, in turn, be part of a seat, a cover or a lounger. Determining the location or, respectively, the orientation of the pelvis is a particularly well-established method, since the position of the ischial tuberosities, the iliac crest, the coccyx or, respectively, the pubic bone can be inferred in a known manner by detecting a few peak pressures. Based on these positions, the size, the location and the orientation of the pelvis can be determined thanks to anatomical considerations, as described in detail in AT 523 112A 1. In particular, by limiting the pelvic configurations that have been rendered possible by a Mandelbrot set, these parameters and thus the reference depiction can be deduced particularly quickly. If, in this method, the deployment sensor is used additionally for determining the reference depiction, it is even possible to measure only two pressure points using the surface sensor, whereby positional information of the deployment sensor can be used as third information for clearly determining the reference depiction.

In a second variant of the method according to the invention, as an alternative or in addition to the surface sensor, the calibration sensor(s) can be applied to predetermined characteristic points of the pelvis and the computing unit can determine a mutual distance between the calibration sensors and, from this, the reference depiction of the pelvis. The method according to the invention can thus also be performed without a seat or, respectively, a surface sensor. For example, two calibration sensors can be applied to two characteristic points of the pelvis, e.g., to the iliac spines, and another calibration sensor or the deployment sensor can be applied to another characteristic point such as the sacrum.

If the position or, respectively, the relative position of the calibration sensors or, if applicable, of the deployment sensor is determined, the reference depiction and thus the original location and the original orientation can be determined therefrom. As already described for the surface sensor, the fact that is exploited is that the size, the location and the orientation of the pelvis are already clearly determined on the basis of knowing three characteristic points.

The computing unit preferably determines a mutual distance between the calibration sensors and the deployment sensor and thereby the location or, respectively, the orientation of the deployment sensor on the reference depiction of the pelvis. As a result, the position of the deployment sensor in the reference depiction-and consequently the change in location or, respectively, orientation of the pelvis-can be determined particularly precisely and, in particular, a thickness of the tissue layer between the pelvic bone and the deployment sensor can be taken into account. Determining the position of the deployment sensor may occur in a known manner, for example, via a field strength measurement if the deployment sensor has an electromechanical transceiver, or perhaps by evaluating an image taken by a camera if the deployment sensor is designed as an optical marker.

As an alternative or in addition to the aforementioned embodiment, the deployment sensor can also be attached to a characteristic point of the pelvis, with information about this characteristic point being stored in the computing unit and the computing unit determining the location or, respectively, the orientation of the deployment sensor on the reference depiction of the pelvis based on this information. For example, the deployment sensor can be attached just above the sacrum or the iliac spine, since only a particularly thin tissue layer is usually present in these places. In such cases, the position of the deployment sensor in the reference depiction is immediately known so that the method can be performed particularly easily.

The translatory change in the spatial position determined by the deployment sensor (if desired) and the rotatory change in the spatial orientation can be converted into a movement of the pelvis using simple mathematical methods, since the position of the deployment sensor remains constant in the reference depiction. For example, the reference depiction of the pelvis can be considered as lying within a sphere, with the deployment sensor preferably being at the centre of the sphere. A translation of the deployment sensor, which has been measured if necessary, then corresponds to a translation of the centre of the sphere and thus of the pelvis, and a measured rotation of the deployment sensor corresponds to a rotation of the sphere about the centre and thus to a rotation of the pelvis. If the deployment sensor is not at the centre of such a sphere, a simple coordinate transformation can be performed in order to infer the movement of the reference depiction or, respectively, the movement of the pelvis from the movement of the deployment sensor.

Furthermore, the method preferably comprises the step of actuating a posture correction device, which is preferably arranged in a seat or in a lounger, based on the determined current orientation of the pelvis. Actuation is performed until a desired predetermined orientation of the pelvis is achieved and usually takes place in the computing unit, which, for this purpose, may also comprise a further external sub-computing unit. Actuation can be designed as a feedback loop, i.e., after initial actuation, the current orientation of the pelvis is again determined, and it is checked as to whether the desired orientation of the pelvis has been achieved. If not, actuation continues or, respectively, is performed differently. Posture correction devices are known per se from the prior art and could be formed, for example, by one or several hydraulically actuatable pillows within a backrest.

In a further preferred embodiment, the method comprises the steps of:

- applying at least one further sensor to the person's body in the area of the spine, with the deployment sensor and the at least one further sensor preferably being connected by means of a strip,
- in the computing unit, determining a relative position of the further sensor with regard to said deployment sensor and/or a relative position with regard to the current orientation and, optionally, the current location of the pelvis,
- optionally, actuating a posture correction device in a seat or in a lounger based on the determined relative position and/or displaying the relative position on a screen.

The method according to the invention can thus be expanded in such a way that a positioning of the spine is also measured, which is achieved by the aforementioned determination of the relative position of the further sensor with regard to the pelvis. This can be exploited, among other things, for actuating the above-mentioned posture correction device in a fully automatic manner in order to correct a faulty posture of the person. In contrast to the above-mentioned embodiment, the posture correction can therefore not only be determined on the basis of a pelvic position, but rather from the combination of pelvic position and spinal position. The determination of the relative position can be done in a suitable manner, such as via a field strength measurement or an optical method. It should be noted that the additional sensor has no influence on the determination of the location and orientation of the pelvis, but only on the determination of the positioning of the spine.

In a further aspect, the invention relates to a system which is designed for performing the above-mentioned method, i.e., a system for continuously determining the orientation (and optionally for determining the location) of a person's pelvis using a single deployment sensor, comprising at least one calibration sensor and the deployment sensor, wherein the deployment sensor can be designed especially for detecting the rotatory change in the spatial orientation and, if applicable, the translatory change in the spatial location of the deployment sensor, the deployment sensor being applicable to the person's body in the area of the pelvis, in particular in the area of a characteristic point of the pelvis such as the pubic bone, the iliac crest or the sacrum, the system furthermore comprising a computing unit which is designed for receiving measured values of the calibration sensor, determining a reference depiction of the pelvis based on the measured values received from the calibration sensor, and storing the current orientation and, if applicable, the current location of the pelvis, the original orientation or, respectively, the original location, with the computing unit furthermore being designed for receiving measured values of the deployment sensor which are representative of the rotatory change in the spatial orientation and, if applicable, of the translatory change in the spatial location of the deployment sensor, and updating the current orientation and, if applicable, the current location of the pelvis based only on the measured values received from the deployment sensor. All embodiments and advantages described for the method are also applicable to the system.

Furthermore, it may be envisaged that the system comprises a strip on which the deployment sensor and at least one further sensor are attached, the at least one further sensor preferably being designed in a way that is structurally identical to the deployment sensor. The strip can be applied, e.g., stuck on, essentially along the spine, with the deployment sensor being attached to the lower end of the strip. This results in a particularly simple simultaneous tracking of the pelvis and the spine, which is barely noticeable to the person.

Advantageous and non-limiting embodiments of the invention are explained in further detail below with reference to the drawings.

Figure 1:
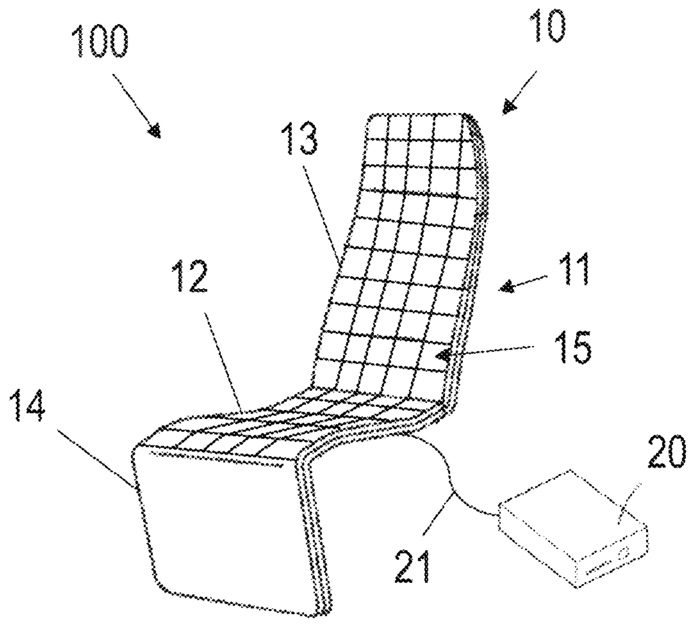
Fig. 1 (Prior art)
FIG. 1 shows a schematic perspective illustration of a seat with an integrated surface sensor according to the prior art.

FIG. 1 shows a device 100 for determining the location and orientation of a pelvis of a person sitting on a seat 10. The seat 10 could alternatively be a cover or a lounger (not illustrated) on which the person lies. The device 100 comprises a computing unit 20 and a surface sensor 11 connected to the computing unit 20. The surface sensor 11 is arranged on a seat element 12 and/or in a back element 13 of the seat 10, especially integrated therein, with a leg element 14 of the seat 10 having no surface sensor 11. In a further embodiment, which is not illustrated, besides the seat element 12 and the back element 13, the leg element 14 can also have a surface sensor 11. In yet further embodiments, which are not illustrated either, only the seat element 12 or the back element 13 can have a surface sensor 11. Said embodiments are combinable, which means that, for example, the leg element 14 and the seat element 12 have a surface sensor 11 and the back element 13 has no surface sensor 11. The surface sensor 11 exemplified in FIG. 1 has large-scale individual sensors 15, for which reason the determination of distances can occur only roughly. However, the surface sensors that are used can also have many more individual sensors in a finer grid or, respectively, array than what is shown in Fig, 1.

In order to achieve high sensitivity of the individual sensors 15, the surface sensor 11 can be shaped in such a way that it adapts at least partially to the person's pelvis. As a result, the surface sensor 11, which is designed for detecting sitting and bearing pressures exerted on the surface sensor 11 by the person's pelvis, coccyx and sacrum, can detect the sitting and bearing pressures with a high level of precision. As can be seen in FIG. 1, the surface sensor 11 is an array of sensors 15 which are selected from the group consisting of mechanical, electrical, pneumatic or hydraulic sensors. In particular, the surface sensor is a two-dimensional array of sensors 15 which completely occupies the seat element 12 and the back element 14 of the seat 10. The number of sensors 15 arranged in the array can vary and is not limited to a specific number. For example, an array with 5×5 sensors 15 could be used. As a result, the position of the sitting and bearing pressures exerted by the person's pelvis, coccyx and sacrum, and thus each position of the person's pelvis, can be determined with sufficient accuracy. The sensors 15 of the surface sensor 11 are preferably designed as flat chambers which are filled with a fluid, for example air or water. In this case, the surface sensor 11 is connected to a computing unit 20 via channels 21. Electrical or mechanical sensors can also be used for detecting the sitting and bearing pressures and are therefore not limited to the sensors previously mentioned as examples. For example, the sensors 15 can also be strain gauges that can be arranged in an array. In this case, the computing unit 20 is electrically connected to the surface sensor 11.

Characteristic points of the pelvis, such as the position of the pubic bone, the coccyx and the sacrum, the ischial tuberosities, the iliac spine or the iliac crest, can be inferred from the pressure points that have been determined. As these characteristic points are located in well-defined positions of the pelvis, a determination of the location and orientation of the pelvis can be performed immediately, for example, via geometric relationships derived from the Mandelbrot set, as is sufficiently known from the prior art.

However, such a device 100 according to the prior art involves the disadvantage that the determination of the location and orientation of the pelvis can be performed only if the person is properly located on the seat 10 and the pressure transmission function, which is dependent, in particular, on the degree of hardness and soft tissue, facilitates appropriate detection of pressure ranges.

Figure 2:
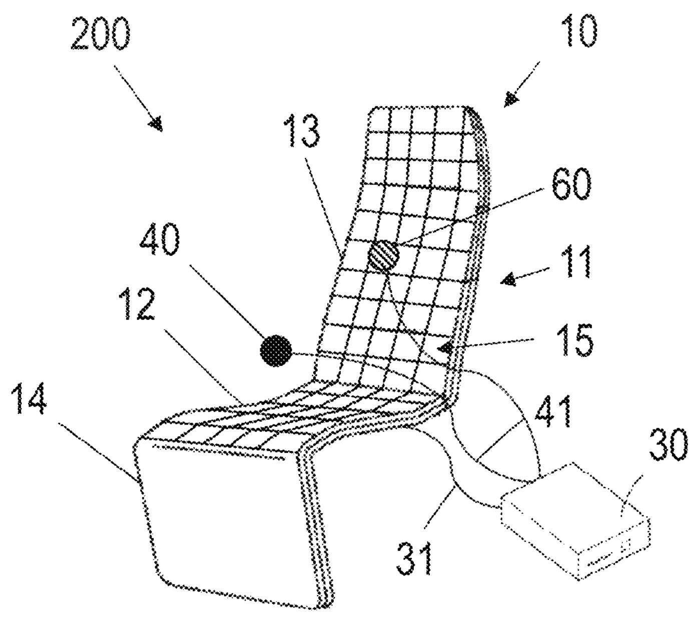
FIG. 2 shows the seat of FIG. 1 with an additional deployment sensor according to the invention in a schematic perspective view.

FIG. 2 shows a system 200 according to the invention wherein the seat 10 illustrated above (or an appropriate cover or lounger, respectively) comprising a surface sensor 11 can be used, with this sensor only being used as a calibration sensor, as will be explained in further detail below. Therefore, the same reference numerals as in FIG. 1 are used also in the system 200 according to the invention of FIG. 2 for the seat 10, the surface element 11 and the other components, and all embodiments described for FIG. 1 can also be applied in the system according to the invention. However, as shown below with reference to FIG. 3, the seat 10 comprising a surface sensor is also not mandatory in the system according to the invention. The surface sensor 11 is used as a calibration sensor in the system 200 and its purpose is to determine a current location and a current orientation of the person's pelvis at a "zero time", i.e., the location thus determined and the orientation thus determined of the pelvis are identified as the original location and the original orientation. This can be done as is known in the prior art, for example, by the surface element 11 determining the characteristic points of the pelvis via pressure points, from which conclusions about the size, location and orientation of the pelvis can be drawn in a known manner. Since this is sufficiently known from the prior art, e.g., from the prior art cited in the introduction to the specification, this will not be addressed any further.

In order to automatically determine the original location and the original orientation of the pelvis, the system comprises a computing unit 30, which is connected to the surface sensor 11 via lines 31, as described above for FIG. 1. The computing unit 30 receives measured values of the calibration sensor and determines a reference depiction of the pelvis based on the measured values received from the calibration sensor. The reference depiction could be, for example, a graphic illustration that is output on a screen, or simply a numerical or, respectively, parameterized depiction of the pelvis that is stored in a volatile or non-volatile memory of the computing unit 30. A simple parameterization can be provided, for example, by storing the positions of three pressure points, e.g., the position of the ischial tuberosities/iliac crest and the position of the sacrum/pubic bone. As is commonly known to those skilled in the art, these positions already parameterize the entire pelvis, including its location and orientation. However, in order to facilitate further calculation, the pelvis could also be parameterized as a sphere, the centre of which is located, for example, in the sacrum of the pelvis, i.e., the reference depiction of the pelvis can be chosen within this sphere.

After the original location and the original orientation of the pelvis have been determined, further dynamic tracking of the pelvis is performed according to the invention by means of a deployment sensor 40, which is attached in the area of the person's pelvis. Herein, "in the area of the pelvis" is understood in the sense that the respective sensor is attached, for example, to the patient's skin directly above the pelvic bone. This also means that the sensor can be attached over the pelvic bone over a larger layer of tissue, e.g., a layer of fat or a muscle. In general, the sensor is therefore attached to a part of the human body which is not connected to the pelvis via a further joint.

The deployment sensor 40 is designed for detecting a translatory change in a spatial location and a rotatory change in a spatial orientation of the deployment sensor 40. The deployment sensor 40 is therefore generally a so-called inertial measurement unit (IMU), usually comprising an acceleration sensor and a rotational speed sensor. The deployment sensor 40 can determine, for example, a forward, sideways or upward translation, in each case viewed with the person as the starting point, or a rotation about a sagittal axis, transverse axis or frontal axis of the person. In particular, the deployment sensor 40 can also determine combined, i.e., concurrent, translation and rotation.

The deployment sensor 40 could also determine the translatory change in a spatial location and a rotatory change in a spatial orientation of a point as result of the fact that the translation or rotation of two points is determined at a predetermined mutual distance. For example, the deployment sensor 40 could thus be formed by the combination of two acceleration sensors 80 at a predetermined distance (see FIG. 6) or of two rotational speed sensors at a predetermined distance. The deployment sensor 40 or the computing unit 30 could convert the translational movement or, respectively, the rotational movement of one of the acceleration sensors or rotational speed sensors, respectively, into a rotational movement or, respectively, translational movement of the respective other acceleration sensor or rotational speed sensor. In particular, a first acceleration sensor can be used for determining the translational movement at the point of the first acceleration sensor, and the translational movement of the other acceleration sensor can be used in combination with the predetermined distance for identifying the rotational movement at the point of the first-mentioned acceleration sensor. Producing the same effect, a first rotational speed sensor can be used for determining the rotational movement at the point of the first rotational speed sensor, and the rotational movement of the other rotational speed sensor can be used in combination with the predetermined distance for identifying the translational movement at the point of the first-mentioned rotational speed sensor. However, it should be mentioned that, even with the combination of two acceleration sensors or, respectively, two rotational speed sensors, there is still a single deployment sensor 40 for detecting a translatory change in a spatial position and a rotatory change in a spatial orientation.

The computing unit 30 receives from the deployment sensor 40 the measuring data for determining the translatory change in a spatial location and the rotatory change in a spatial orientation of the deployment sensor 40. As already explained, the measuring data can be just a translation and a rotation or two different translations or rotations. Afterwards, the computing unit 30 can optionally perform a coordinate transformation depending on the place where the deployment sensor 40 is located on the pelvis, and can convert the translation and rotation of the deployment sensor 40 into a translation and rotation of the pelvis. For this purpose, the original location and the original orientation determined by the calibration sensor can initially be used, and the measuring data supplied by the deployment sensor 40 can be applied to this original location and this original orientation, optionally using a coordinate transformation, and the current location and the current orientation of the pelvis can be updated continuously.

The update of the current location and the current orientation of the pelvis through the deployment sensor 40 can be used to enable the location and orientation of the pelvis to be tracked using only a single sensor 40, even if the person gets up from said seat 10 or, as described below, removes other calibration sensors 50.

The deployment sensor 40 can, but does not have to, be applied to characteristic points of the pelvis such as the pubic bone, the iliac crest, the iliac spines or the sacrum. This simplifies in particular the spatial allocation of the deployment sensor 40 on the reference depiction used by the computing unit 30. For example, as described above, the computing unit 30 determines characteristic points of the pelvis such as the ischial tuberosities/iliac crest and the sacrum/pubic bone/iliac spine. The size and shape of the pelvis can already be determined from this on the basis of anatomical considerations, as is known per se to those skilled in the art. If the deployment sensor 40 is now attached to a characteristic point of the pelvis, such as the sacrum, the pubic bone, the iliac crest or even the iliac spine, the computing unit 30 immediately knows where the deployment sensor 40 is located on the pelvis or, respectively, in the reference depiction, and the translation or, respectively, rotation of the deployment sensor 40 can be converted into a translation or rotation of the pelvis. If the deployment sensor 40 is located, for example, on the pelvis in the area of the sacrum, a rotation of the deployment sensor can be directly converted into a rotation of the reference depiction around the point that is located in the sacrum. If the reference depiction of the pelvis is chosen to be a sphere the centre of which is located in the sacrum, the rotation of the deployment sensor corresponds to a rotation of the sphere around its centre.

However, if the deployment sensor 40 is attached to the pelvis in the area of the iliac spine, a mere rotation of the deployment sensor will result in a combined rotation and translational movement of a sphere having its centre in the sacrum. Such geometric considerations and corresponding coordinate transformations can easily be implemented by a person skilled in the art.

In the above-described embodiment, the computing unit 30 has, for example, an interface which can be used for entering the place where the deployment sensor 40 is applied, e.g., the sacrum, right or left iliac spines, etc. However, the geometric allocation of the position of the deployment sensor 40 to the reference depiction in the computing unit 30 could also be automated, for example, when a relative position of the deployment sensor 40 with regard to the respective calibration sensor is determined. For example, the deployment sensor 40 could output or receive an electromechanical signal, and the position of the deployment sensor 40 could be determined by a field strength that has been measured. For example, the deployment sensor 40 could be designed as an RFID transmitter and/or an RFID receiver.

Determinations of position using such sensors are well known to those skilled in the art. The position of the calibration sensor(s) could also be determined in this way so that the exact position of the deployment sensor 40 in relation to the reference depiction can be known in the computing unit 30, which can facilitate coordinate transformation. In case of the surface sensor 11, it would be possible, for example, to determine at what height (and/or at what longitude or, respectively, latitude) the deployment sensor 40 is located above the surface sensor 11, for which purpose an appropriate electromechanical sensor such as an RFID transmitter and/or an RFID receiver can also be installed in or, respectively, on the surface sensor 11. In such embodiments, it is therefore also not essential for the deployment sensor 40 to be applied to a characteristic point of the pelvis, but the deployment sensor 40 could also be attached, for example, at an arbitrary place such as to the side of the pelvis, and the computing unit could, for instance, automatically detect a relative position of the sacrum with regard to the deployment sensor 40, for example.

Figure 3:
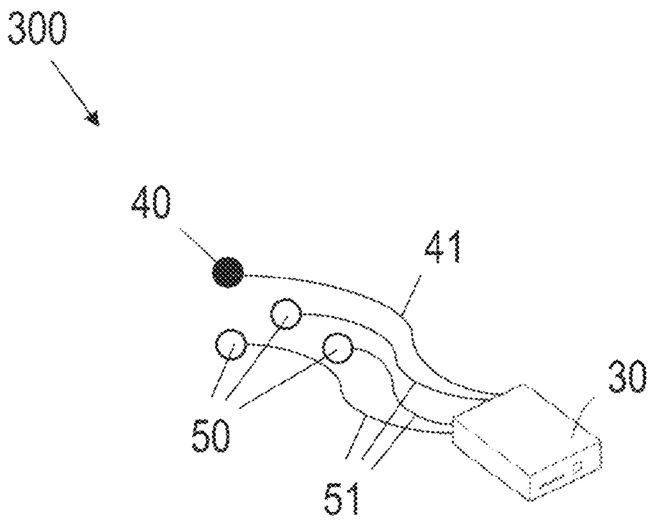
FIG. 3 shows a further system according to the invention in a schematic perspective view.

In FIG. 3, an embodiment according to the invention of a system 300 is shown, wherein a seat 10 comprising a surface sensor 11 is not used, but the original location and the original orientation of the pelvis are determined in a different way. In doing so, several calibration sensors 50, which are point-shaped, for example, are applied to predetermined characteristic points of the pelvis, and the computing unit 30 determines a mutual distance between the calibration sensors 50 and, from this, the reference depiction of the pelvis, for example using measured values of the calibration sensors 50, which have been received via lines 51. The determination of the mutual distance can occur, as above, for the deployment sensor 40 or in a different way. These calibration sensors 50 could themselves also be inertial measurement units, and the geometry of the pelvis could be determined from corresponding measured values. The calibration sensors 50 could also merely be optical markers, and images of the pelvis could be taken with these markers so that the mutual distance of the markers can be determined from the images. In the computing unit, the positions of the sensors are used for generating the reference depiction. Such determinations for determining the reference depiction or, respectively, the original location and the original orientation are known per se to those skilled in the art or are at least easy to implement. The purpose of these calibration sensors 50 is also merely the initial determination of the reference depiction, and further tracking is performed with said deployment sensor 40. It will be appreciated that measuring data of the deployment sensor 40 could also be used for determining the original location or, respectively, the original orientation. For example, only two of the point-shaped calibration sensors 50 could be used, and the computing unit 30 determines the reference depiction, including the original location and the original orientation, from the measured values of the two calibration sensors 50 and the deployment sensor 40, wherein further dynamic tracking of the pelvis occurs based only on the measuring data of the deployment sensor 40, i.e., the calibration sensors 50 could also be removed.

However, the calibration sensors 50 of FIG. 3 which are to be applied to the person do not have to be designed so as to be point-shaped, but could also have a strip-shaped or flat design and could be stuck, for example, over an area of the pelvis which may also comprise several characteristic points of the pelvis. Furthermore, such calibration sensors 50 to be applied to the person could also be combined with a surface sensor 11, as shown in FIG. 2, in order to obtain a more precise reference depiction.

It is thus evident from the synopsis of FIGS. 2 and 3 that it is essentially irrelevant by which means the initial reference depiction, including the original location and the original orientation, is determined. Applying the calibration sensor could, for example, also be understood as stopping an ultrasonic sensor in order to generate the initial reference depiction, with further tracking of the pelvis again occurring with the deployment sensor 40. All connections between sensors and the computing unit as described herein can be wired via lines 31, 41, 51 or be wireless, e.g., via Bluetooth or another communication standard.

Figure 4:
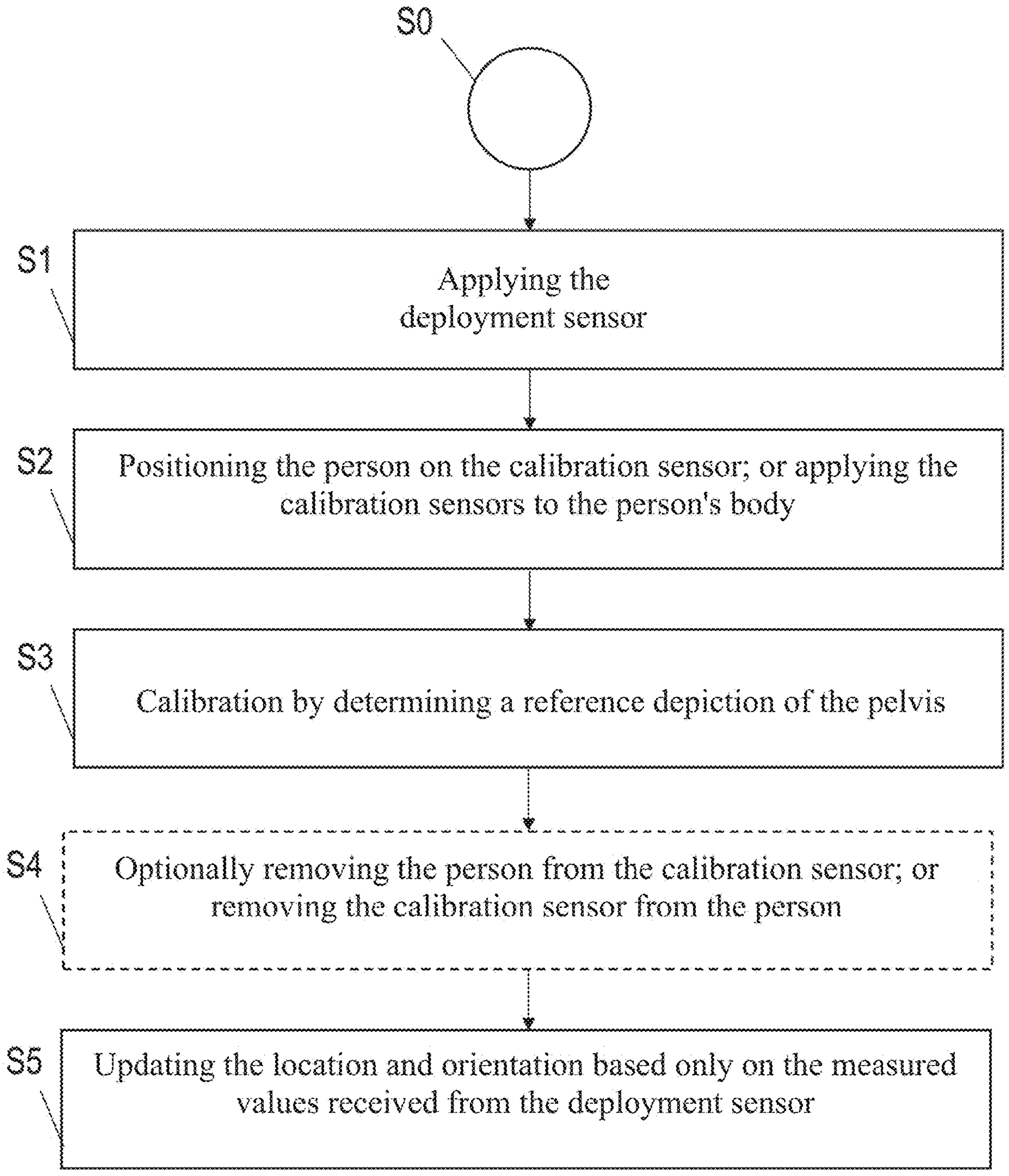
FIG. 4 shows the steps of the method according to the invention in a block diagram.

The method according to the invention will now be described again with reference to FIG. 4. Initially, one or several calibration sensors is/are provided in a step S0. In step S1, the deployment sensor 40 is applied to the person's body in the area of the pelvis. In step S2, the person positions him-or herself on the at least one calibration sensor, e.g., if the calibration sensor is designed as a surface sensor 11 on a seat 10, a lounger or a cover. Alternatively or additionally, in step S2, the calibration sensors 50 are applied to the person's body in the area of the pelvis, as illustrated, for example, in FIG. 3.

In step S3, the computing unit 30 determines the reference depiction of the pelvis based on the measuring data received from the calibration sensors 11, 50, and, optionally, also taking into account the measuring data received from the deployment sensor 40. Furthermore, the computing unit 30 stores the current location and the current orientation of the pelvis according to the reference depiction as the original site and the original position.

At this point, it should be noted that step S1 can take place before step S2 or even after step S2 or S3. However, at the time when the original location and the original position are stored, the computing unit can preferably also receive a "zero signal" of the deployment sensor 40 in order to calibrate the latter relative to the original location and the original position. It is thus preferred if the deployment sensor 40 is attached to the person's body at least at the time when the original location and the original position are stored.

Optionally, in a step S4, after the reference depiction has been generated and the original location and the original position have been stored, the calibration sensors 50 can be removed or, respectively, the person can get up from the seat 10 comprising the surface sensor, as these measuring data are no longer needed.

In step S5, which takes place simultaneously with, before or after step S4, the computing unit 30 receives the measured values of the deployment sensor 40, comprising the translatory change in the spatial location and the rotatory change in the spatial orientation, and converts them into a translatory change in the spatial location and the rotatory change in the spatial orientation of the reference depiction, optionally using a coordinate transformation, so that the computing unit can update the current location and the current orientation of the pelvis based only on the measured values received from the deployment sensor.

This method can be used, for example, for displaying a graphic illustration of the dynamic change in the location or, respectively, orientation of the pelvis (with measuring points of the spine that can be expanded as required) on a screen, for example during physical therapy.

Alternatively or additionally, in response to the current location or, respectively, the current orientation, control elements such as a posture correction device on a seat, lounger or cover on which the person is located could be actuated automatically in order to automatically correct the position or, respectively, posture of the person, for example, automated patient positioning management could be supported in this way using a single sensor.

Furthermore, the system 200, 300 or, respectively, the corresponding method can be used for combining the current location and the current orientation of the pelvis with other measuring systems, such as a measured posture of the spine, which is achieved, for example, by at least one further sensor 60 being applied to the person's body in the area of the spine, which could be designed, for example, as an inertial measurement unit like the aforementioned deployment sensor 40. The further sensor 60 is shown schematically in FIG. 3, but can also be combined with all other embodiments. The further sensor 60 can be point-shaped and can be attached, for example, between the shoulder blades or in the area of a predetermined vertebra. In particular, a further sensor 60 or several further sensors 60 can also be arranged, in each case, in the area of the spinous processes of one or more vertebrae, in particular of the three lower lumbar vertebrae L3, L4 and L5. Since the position of the spinous processes, in particular of the three lower lumbar vertebrae, is based on an ideal in relation to the remaining characteristics of the pelvis, this information can also be used for providing feedback about a body posture that is correct or needs to be corrected, respectively. The ideal position could be determined, for example, from the first iterations or, respectively, their boundary curves of a Mandelbrot set, which has been determined by means of a surface sensor 11. Furthermore, a measuring strip could also be used, which is applied along the spine and covers several spinous processes so that the curvature of the spine can also be measured precisely.

The computing unit 30 can then determine a relative position between the further sensor 60 and the deployment sensor 40 and/or a relative position between the further sensor 60 and the current location and the current orientation of the pelvis (e.g., the centre of the aforementioned sphere). Via this relative position, it can be determined as to whether the person is sitting upright, for example. If the relative position is, e.g., too low, the conclusion can be that there is a hunched posture.

The relative position can be used for displaying the posture of the spine on a screen, for example in the course of a physical therapy, or, based on the determined relative position, the computing unit 30 can directly actuate a posture correction device in a seat or in a lounger in order to correct the person's posture. The posture correction device can be, for example, an inflatable or fillable pillow in the backrest of a seat.

Figure 5:
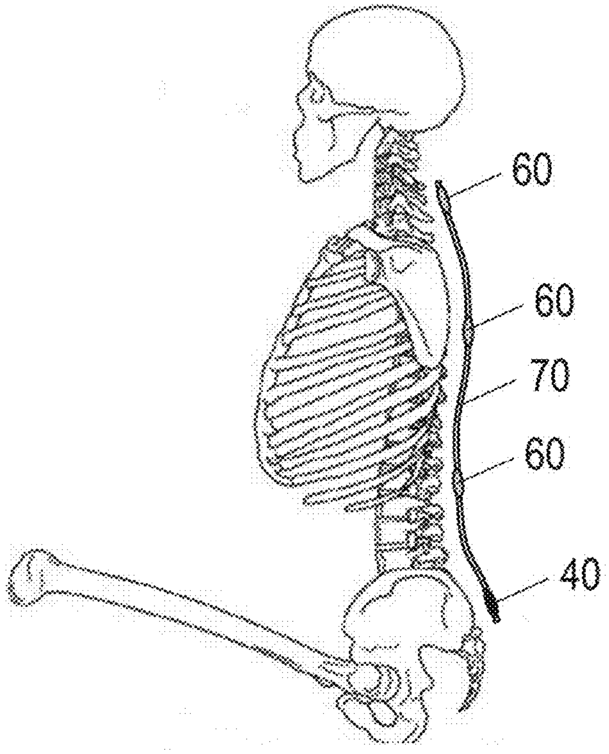
FIG. 5 shows a measuring strip in which the deployment sensor according to the invention is used.

FIG. 5 shows a practical implementation of the deployment sensor 40 in combination with three further sensors 60, although more or fewer further sensors 60 can also be used. The deployment sensor 40 and the further sensors 60 are attached in or on a strip 70, whereby the respective relative position, i.e., the distance, from the deployment sensor 40 to the next one of the further sensors 60 or, respectively, from one of the further sensors 60 to the next one of the further sensors 60 is predefined. These distances can be stored, for example, in the computing unit 30 or, respectively, they can be fed into the computing unit 30 after the strip 70 has been applied and the distances have been measured.

In this system with strips 70, the deployment sensor 40 again serves for tracking the orientation of the pelvis, while the further sensors 60 serve for tracking the orientation of the spine. In this case, the further sensors 60 can be applied to characteristic points of the spine, e.g., on certain vertebrae. Usually, the deployment sensor 40 is thereby attached to one end of the strip 70 so that the strip 70 can extend from the pelvis, where the deployment sensor 40 is attached, across the spine.

In the illustrated embodiment of FIG. 5, the further sensors 60 are designed in a way that is structurally identical to the deployment sensor 40, but this, however, is not mandatory. The strip 70 usually comprises an adhesive strip to be attached to the person's back. The strip could be designed as a simple carrier material or perhaps with lines connecting the sensors 40, 60. A common line could then be routed to the computing unit or to a transceiver, which, in turn, communicates with the computing unit 40.

Figure 6:
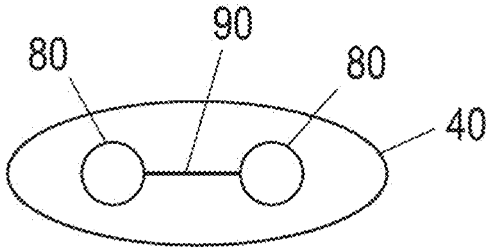
FIG. 6 shows a preferred embodiment variant of the deployment sensor.

FIG. 6 shows a particularly preferred example of a practical structure of a deployment sensor 40. This deployment sensor 40 is designed in that two acceleration sensors 80 are arranged at a predetermined distance from each other, e.g., 2 cm or more generally, e.g., 1 cm to 5 cm.

As already explained above, the acceleration sensors 80 can, in each case, determine only one translational movement. However, since the mutual distance of the acceleration sensors 80 is known, the translational movement of one of the acceleration sensors 80 can be converted into a rotational movement so that rotation and translation of the pelvis can be tracked. In the illustrated example, the acceleration sensors are separated by a physical spacer 90, although this is not mandatory and the distance can be permanently specified due to the manufacture of the deployment sensor 40. In the embodiment of FIG. 5, the distance of the acceleration sensors 80 can be chosen in parallel with the strip 70. As already mentioned, the further sensors 60 in FIG. 5 can be designed in the same way as this deployment sensor 40.

Something that has always been addressed in the above-mentioned embodiments is that the system 200, 300 tracks both the current location and the current orientation of the pelvis.

However, in simpler embodiments, it could also be envisaged that only the current orientation of the pelvis is tracked, i.e., the current location of the pelvis is not tracked in other embodiments. In the simplest case, the deployment sensor 40 can thus only be a rotational speed sensor, or a combination of two acceleration sensors from which a rotation is determined. Therefore, the calibration sensor also does not need to determine the original location, and determining the location within the computing unit 30 can be omitted if only the orientation of the pelvis is to be tracked.

The invention claimed is:

1. A method of continuously determining the orientation of a person's pelvis, comprising:

applying a deployment sensor to the person's body in an area of the pelvis, positioning the person on a calibration sensor or applying the calibration sensor to the person, in a computing unit, receiving measured values of the calibration sensor and determining a reference depiction of the pelvis based on the measured values received from the calibration sensor, with a current orientation of the pelvis determined from the reference depiction being stored as an original orientation, in the computing unit, receiving measured values of the deployment sensor, and updating the current orientation of the pelvis based only on the measured values received from the deployment sensor by applying the measured values from the deployment sensor to the stored original orientation, and actuating a posture correction device, which is arranged in a seat or in a lounger, based on the updated current orientation of the pelvis.

2. The method according to claim 1, wherein the method is furthermore performed for continuously determining a location of the person's pelvis, the deployment sensor being designed for determining a translatory change in a spatial position and a rotatory change in a spatial position, wherein, after determining the reference depiction of the pelvis based on the measured values received from the calibration sensor, a current location of the pelvis is stored as an original location, and, after receiving measured values of the deployment sensor, an update of the current location of the pelvis is performed in the computing unit based only on the measured values received from the deployment sensor.

3. The method according to claim 1, wherein the calibration sensor comprises a surface sensor, with the surface sensor determining the position of two characteristic points from measured pressure readings and, from this, the reference depiction, the surface sensor being part of a seat element and/or a back element.

4. The method according to claim 1, wherein a further calibration sensor is applied to a predetermined characteristic point of the pelvis and the computing unit determines a distance between the calibration sensor and the further calibration sensor and, from this, the reference depiction of the pelvis.

5. The method according to claim 1, wherein the computing unit determines a distance between the calibration sensor and a further calibration sensor and the orientation of the deployment sensor on the reference depiction of the pelvis.

6. The method according to claim 1, wherein the deployment sensor is attached to a characteristic point of the pelvis, information about the characteristic point is stored in the computing unit and the computing unit determines an orientation of the deployment sensor on the reference depiction of the pelvis based on this information.

7. The method according to claim 1, wherein the computing unit determines the reference depiction of the pelvis within a sphere, a centre of the sphere is located in the sacrum of the pelvis, wherein a rotatory change in a spatial orientation of the deployment sensor is converted into a rotatory change in a spatial orientation of the sphere and a translatory change in a spatial position of the deployment sensor is converted into a translatory change in a spatial position of the sphere.

8. The method according to claim 1, further comprising:

applying a further sensor to the person's body in an area of the spine, the deployment sensor and the further sensor being connected by a strip, in the computing unit, determining a relative position of the further sensor with regard to the deployment sensor, and actuating the posture correction device, based on the determined relative position, and/or displaying the relative position on a screen.

9. A system for continuously determining the orientation of a person's pelvis using a single deployment sensor, comprising:

a calibration sensor and the deployment sensor, the deployment sensor being applicable to the person's body in the area of the pelvis, and a computing unit operable to receive measured values of the calibration sensor and determine a reference depiction of the pelvis based on the measured values received from the calibration sensor, with a current orientation of the pelvis determined from the reference depiction being stored as an original orientation, and receive measured values of the deployment sensor, and update the current orientation of the pelvis based only on the measured values received from the deployment sensor by applying the measured values from the deployment sensor to the stored original orientation, wherein the computing unit is operable to actuate a posture correction device based on the updated current orientation of the pelvis.

10. The system according to claim 9, wherein the system is operable to continuously determine a location of the person's pelvis, with the deployment sensor operable to determine a translatory change in a spatial position and a rotatory change in a spatial position, with the computing unit being operable, after determining the reference depiction of the pelvis based on the measured values received from the calibration sensor, to also store a current location of the pelvis as an original location, and also, after receiving measured values of the deployment sensor, to perform an update of the current location of the pelvis based only on the measured values received from the deployment sensor.

11. The system according to claim 9, wherein the deployment sensor is a point-shaped sensor, and comprises only a rotational speed sensor or only a combination of a rotational speed sensor with an acceleration sensor.

12. The system according to claim 9, wherein the system comprises a strip on which the deployment sensor and a further sensor are attached, the further sensor having structure that is identical to a structure of the deployment sensor.

13. The system according to claim 9, wherein the calibration sensor comprises a surface sensor, wherein the system further comprises a seat with a seat element and/or a back element, the surface sensor being part of the seat element and/or the back element.

14. The system according to claim 9, wherein the system comprises a further calibration sensor applicable to a predetermined characteristic point of the pelvis, and the computing unit is operable to determine a distance between the calibration sensor and the further calibration sensor and, from this, the reference depiction of the pelvis.

* * * * *